United States Patent
Brotchie et al.

(10) Patent No.: US 10,736,909 B2
(45) Date of Patent: Aug. 11, 2020

(54) USE OF TREHALOSE FOR TREATMENT OF NEUROLOGICAL DISEASES

(71) Applicant: JUNAXO, INC., Toronto, ON (CA)

(72) Inventors: Jonathan Michael Brotchie, Montreal (CA); Patrick Alexander Howson, Toronto (CA)

(73) Assignee: JUNAXO, INC., Toronto, Ontario (CA)

( * ) Notice: Subject to any disclaimer, the term of this patent is extended or adjusted under 35 U.S.C. 154(b) by 0 days.

(21) Appl. No.: 16/076,468

(22) PCT Filed: Feb. 3, 2017

(86) PCT No.: PCT/CA2017/050123
§ 371 (c)(1),
(2) Date: Aug. 8, 2018

(87) PCT Pub. No.: WO2017/136922
PCT Pub. Date: Aug. 17, 2017

(65) Prior Publication Data
US 2019/0046549 A1    Feb. 14, 2019

Related U.S. Application Data

(60) Provisional application No. 62/292,505, filed on Feb. 8, 2016.

(51) Int. Cl.
| | |
|---|---|
| *A61K 31/7016* | (2006.01) |
| *A23L 33/125* | (2016.01) |
| *A61P 25/28* | (2006.01) |
| *A61P 25/16* | (2006.01) |

(52) U.S. Cl.
CPC ........ *A61K 31/7016* (2013.01); *A23L 33/125* (2016.08); *A61P 25/16* (2018.01); *A61P 25/28* (2018.01); *A23V 2002/00* (2013.01); *A23V 2200/322* (2013.01); *A23V 2250/636* (2013.01)

(58) Field of Classification Search
CPC ....... A61K 31/7016; A61P 25/28; A61P 25/16
See application file for complete search history.

(56) References Cited

U.S. PATENT DOCUMENTS

| 4,762,857 A * | 8/1988 | Bollin, Jr. ............ A61K 9/1694 424/465 |
| 2006/0073255 A1* | 4/2006 | Catani .................... A23L 27/34 426/548 |
| 2016/0022716 A1 | 1/2016 | Megiddo |

FOREIGN PATENT DOCUMENTS

| CA | 2608198 | 11/2006 | |
| WO | WO-2004047565 A1 * | 6/2004 | ........... A61K 31/198 |
| WO | 2014065606 | 5/2014 | |
| WO | 2014171333 | 11/2014 | |
| WO | 2014181333 | 11/2014 | |
| WO | 2015108372 | 7/2015 | |

OTHER PUBLICATIONS

Richards et al., Food and Chemical Toxicology, 2002, 40, p. 871-898. (Year: 2002).*
Google Machine Translation of WO 2004/047565, https://patents.google.com/patent/WO2004047565A1, accessed online on Mar. 16, 2020. (Year: 2020).*
International Search Report of the parent PCT/CA2017/050123 dated May 19, 2017.
Ross et al., "Protein aggregation and neurodegenerative disease", Nature Medicine, Jul. 2004, vol. 10, pp. S1-S17.
Ferguson et al., Behav Brain Res., 2015, 292, pp. 68-78.
Sarkar et al., Neurotoxicology, 2014, 44, 250-262.
Wu et al., Neuroscience, 2015, 284, pp. 900-911.
He et al., Mol Neurobiol., 2015, DOI 10.1007/s12035-015-9173-7.
Tanji et al., Biochem Biophys Res Commun., 2015, 465, pp. 746-752.
Wang and Hay, Front Neurosci., 2015, 9, pp. 1-8.
Emanuele, Curr Drug Targets, 2014, 15, pp. 551-557.
Kiriyama and Nochi, Int J Mol Sci., 2015, 16, pp. 26797-26812.
Rubinsztein et al, J Exp Med., 2015, 212, pp. 979-990.
Richards et al, In : "Alternative sweeteners", Jan. 1, 2001. Marcel Dekker, XP055610913, p. 456.

* cited by examiner

*Primary Examiner* — Jonathan S Lau
(74) *Attorney, Agent, or Firm* — Hill & Schumacher

(57) ABSTRACT

The present disclosure discloses trehalose for use in treatment of neurological disorders, wherein the trehalose is for a single daily administration with the daily dose between about 0.25 to about 12.5 g/kg/day. The daily dose may be about 2.67 g/kg/day. A method for treating a neurological disorders is disclosed which involves administering trehalose to a subject as a single daily administration with a daily dose between about 0.25 to about 12.5 g/kg/day and in an embodiment of this method the daily dose is about 2.67 g/kg/day. Also disclosed herein is the use of trehalose in the manufacture of a medicament for treatment of neurological disorders, wherein the trehalose is formulated as a single daily dose with the trehalose present in the medicament in an amount of between about 0.25 to about 12.5 g/kg/day. In an embodiment the daily dose is about 2.67 g/kg/day. The present disclosure provides a pharmaceutical composition for treating neurological disorders, comprising a daily dose of trehalose, and a pharmaceutically acceptable carrier wherein the daily dose of the trehalose is between about 0.25 to about 12.5 g/kg. The trehalose may be formulated as part of a foodstuff.

20 Claims, 2 Drawing Sheets

USE OF TREHALOSE FOR TREATMENT OF NEUROLOGICAL DISEASES

FIELD

The present disclosure relates to the use of trehalose for the treatment of neurological disorders, including but not limited to Parkinson's disease (PD).

BACKGROUND

Autophagy is a natural, conserved, process that allows the orderly degradation of cytoplasmic contents. There are three pathways of autophagy, macroautophagy, microautophagy and chaperone-mediated autophagy, of which macroautophagy is the main pathway. Autophagy plays several roles in cellular functioning including the breakdown and recycling of proteins, the degradation of infectious particles and the removal of damaged organelles, cell membranes and proteins. In certain diseases, called proteinopathies, accumulation of structurally abnormal proteins disrupts normal cellular function. There is a wide range of proteinopathies including many neurodegenerative disorders such as Parkinson's disease, Alzheimer's disease and amyotrophic lateral sclerosis. Strategies aimed at limiting the accumulation of the abnormal proteins, such as enhancing the removal of abnormal proteins, are being investigated as potential therapies for proteinopathies including neurodegenerative disorders. For reviews on autophagy and neurodegenerative disorders see Rubinsztein et al, J Exp Med., 2015, 212, pp. 979-990; Kiriyama and Nochi, Int J Mol Sci., 2015, 16, pp. 26797-26812.

Trehalose is a disaccharide that represents one such strategy to reduce the accumulation of abnormal proteins. The exact mechanism of action of trehalose is not known, however, it possesses several properties that may be useful in preventing neurodegeneration including stabilizing proteins, acting as a chemical chaperone for misfolded proteins and improving the clearance of abnormal proteins (for a review see Emanuele, Curr Drug Targets, 2014, 15, pp 551-557). Trehalose reduces levels of α-synuclein (αSYN), the protein which is misfolded in PD and drives the pathophysiology of the disease (for review see Wang and Hay, Front Neurosci., 2015, 9, pp 1-8), in rodent models of PD (Tanji et al., Biochem Biophys Res Commun., 2015, 465, pp746-752; He et al., Mol Neurobiol., 2015, DOI 10.1007/s12035-015-9173-7; Wu et al., Neuroscience, 2015, 284, pp 900-911).

There are several published papers showing the benefit of trehalose in animal models of PD when the trehalose is dissolved in the animal drinking water such that it is constantly available to the animals. These are summarized in Table 1 below.

TABLE 1

| Model | Trehalose administered | Effect | Reference |
|---|---|---|---|
| MPTP-lesioned mouse | 2% trehalose in drinking water | Neuroprotection observed | Sarkar et al., Neurotoxicology, 2014, 44, 250-262. |
| Rotenone-lesioned rat | 2% trehalose in drinking water | Neuroprotection observed | Wu et al., Neuroscience, 2015, 284, pp 900-911 |
| AAV α-synuclein rat | 2 and 5% in drinking water | Neuroprotection observed | He et al., Mol Neurobiol., 2015, DOI 10.1007/s12035-015-9173-7. |
| Chronic MPTP-lesioned mouse | 1% in the drinking water | No behavioural effect. Some effect on dopamine levels | Ferguson et al., Behav Brain Res., 2015, 292, pp 68-78. |
| Transgenic α-synuclein mouse | 2% trehalose in drinking water | Increased autophagy | Tanji et al., Biochem Biophys Res Commun., 2015, 465, pp746-752. |

These studies demonstrate the potential of trehalose as a treatment for PD. However, the most efficacious method of administering trehalose is unknown and uninvestigated with trehalose administered in the drinking water in all these studies. Similarly, whilst there are several papers in the literature showing a positive effect of trehalose in animal models of other neurodegenerative proteinopathies (e.g. Alzheimer's disease, amyotrophic lateral sclerosis and Huntington's disease) trehalose was administered in the drinking water.

Canadian Patent No. CA2608198 A1 (Lindquist et al., 2006) discloses a method of inhibiting α-synuclein-mediated cellular toxicity by contacting a cell expressing a toxicity-inducing amount or form of α-synuclein with an effective amount of an osmolyte, in which the osmolyte is trehalose.

As noted above, in all the previous work performed in animal models of PD, trehalose has been administered to animals as a solution in their drinking water. Furthermore, no fully quantitative methods have been used to measure trehalose levels in either the plasma or brain in these studies.

Determining the best dosage regime and methodology for delivery of the trehalose to give the most efficacious treatment of neurological disorders would be very beneficial. With a rapidly aging population, and with the cost of health care treatment increasing rapidly as a result, finding an economical and simple method of treating a wide variety of neurological disorders, including PD, would be very advantageous.

SUMMARY

The present disclosure provides a pharmaceutical kit comprising:
- trehalose for treatment of neurological disorders, and
- instructions for a single daily administration of the trehalose with the daily dose being between about 0.25 to about 12.5 g/kg/day.

A preferred range of trehalose is between about 0.5 to about 10 g/kg/day. A more preferred range of trehalose is between about 0.75 to about 7.5 g/kg/day. A more preferred amount is about 2.67 g/kg/day.

Disclosed herein is trehalose for use in the treatment of neurological disorders, wherein the trehalose is administered as a single daily administration with the daily dose between about 0.25 to about 12.5 g/kg/day. In an embodiment the daily dose is about 2.67 g/kg/day.

Disclosed herein is a method for treating neurological disorders, comprising:
administering trehalose to a subject as a single daily administration with a daily dose between about 0.25 to about 12.5 g/kg/day. In an embodiment of this method the daily dose is about 2.67 g/kg/day.

Also disclosed herein is the use of trehalose in the manufacture of a medicament for treatment of neurological disorders, wherein the trehalose is formulated as a single daily dose with the trehalose present in the medicament in an amount of between about 0.25 to about 12.5 g/kg/day. In an embodiment the daily dose is about 2.67 g/kg/day.

The present disclosure provides a pharmaceutical composition for treating neurological disorders, comprising a daily dose of trehalose, and a pharmaceutically acceptable carrier wherein the daily dose of the trehalose is between about 0.25 to about 12.5 g/kg. In an embodiment the daily dose is about 2.67 g/kg/day.

The present disclosure provides a "foodstuff", "food supplement", "beverage" or "beverage supplement" composition, where "foodstuff", "food supplement", "beverage" or "beverage supplement" have normal meanings for those terms and are not restricted to pharmaceutical preparations, for treating neurological disorders, comprising a daily dose of trehalose, and a dietary acceptable carrier wherein the daily dose of the trehalose is between about 0.25 to about 12.5 g/kg. In an embodiment of the daily dose is about 2.67 g/kg/day. Examples of "foodstuffs", "food supplements", "beverages" or "beverage supplements" include, but are not limited to, processed foods, ingredients added to prepared foodstuffs and beverages (e.g. cooking ingredients, sweeteners), energy bars, baked goods, protein-shakes, soft-drinks and alcoholic drinks.

The present disclosure provides a "Medical food" as defined in the Food and Drug Administration's 1988 Orphan Drug Act Amendments for treating neurological disorders, comprising a daily dose of trehalose, and a dietary acceptable carrier wherein the daily dose of the trehalose is between about 0.25 to about 12.5 g/kg. In an embodiment of the daily dose is about 2.67 g/kg/day. Medical foods are foods that are specially formulated and intended for the dietary management of a disease that has distinctive nutritional needs that cannot be met by normal diet alone.

Medical foods are distinct from the broader category of foods for special dietary use and from traditional foods that bear a health claim. In order to be considered a medical food the product must, at a minimum (i) be a food for oral ingestion or tube feeding (nasogastric tube), (ii) be labeled for the dietary management of a specific medical disorder, disease or condition for which there are distinctive nutritional requirements, and (iii) be intended to be used under medical supervision.

The neurological disorders are any one or combination of PD, synucleinopathies and proteinopathies. The synucleinopathies are any one of PD with dementia, dementia with Lewy bodies, MSA, essential tremor, Gaucher disease and other lysosomal storage disorders, and neurodegeneration with brain iron accumulation. The proteinopathies include Alzheimer's disease, cerebral β-amyloid angiopathy, retinal ganglion cell degeneration in glaucoma, prion diseases, tauopathies, frontotemporal lobar degeneration, FTLD-FUS, amyotrophic lateral sclerosis (ALS), Huntington's disease and other triplet repeat disorders, familial British dementia, familial Danish dementia, hereditary cerebral hemorrhage with amyloidosis, CADASIL, Alexander disease, seipinopathies, familial amyloidotic neuropathy, serpinopathies and retinitis pigmentosa with rhodopsin mutations.

Also disclosed herein is the use of trehalose in the manufacture of a medicament for treatment of neurological disorders, wherein the trehalose is formulated as a single daily dose with the trehalose present in the medicament in an amount of between about 0.25 to about 12.5 g/kg/day.

The present disclosure provides a pharmaceutical composition for treating neurological disorders, comprising a daily dose of trehalose, and a pharmaceutically acceptable carrier wherein the daily dose of the trehalose is between about 0.25 to about 12.5 g/kg.

A further understanding of the functional and advantageous aspects of the invention can be realized by reference to the following detailed description.

BRIEF DESCRIPTION OF DRAWINGS

The following is a description of the use of trehalose for treatment of neurological diseases, reference being had to the accompanying drawings, in which.

DETAILED DESCRIPTION

Figure 1:
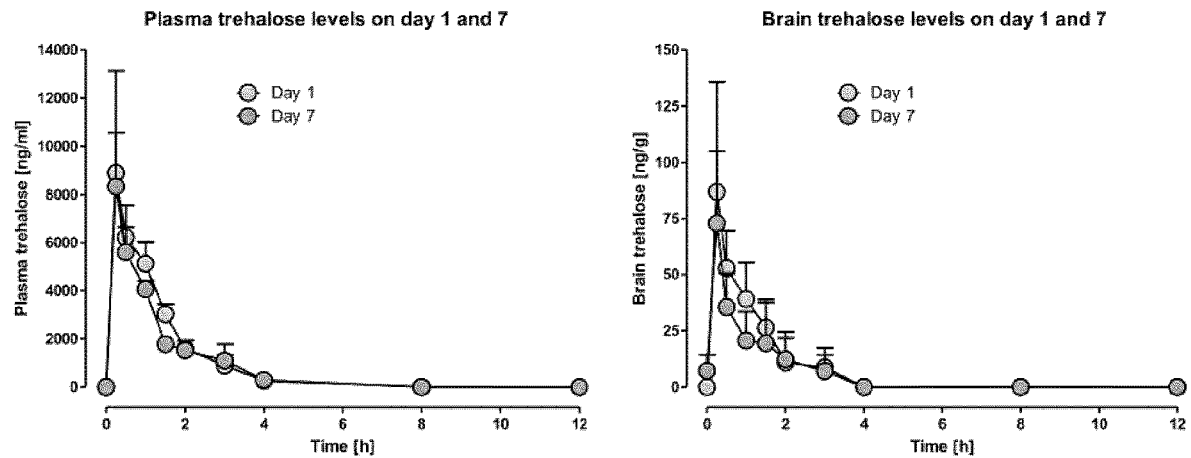
FIG. 1 shows the timecourse of trehalose exposure in the plasma and brain of rats following 1 and 7 days oral administration of trehalose (2.67 g/kg/day, p.o. administered as a single bolus dose).

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dosage ranges to give a few examples.

As use herein, the word "trehalose" refers to the molecule shown in Formula 1 below.

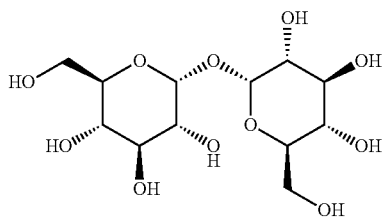

FORMULA 1

Trehalose is also known by other names including "α,α-trehalose"; "α-D-glucopyranosyl-(1→1)-α-D-glucopyranoside". Its IUPAC name is "(2R,3S,4S,5R,6R)-2-(Hydroxymethyl)-6-[(2R,3R,4S,5S,6R)-3,4,5-trihydroxy-6-(hydroxymethyl)oxan-2-yl]oxyoxane-3,4,5-triol". The CAS no. of trehalose is 99-20-7 (anhydrous) 6138-23-4 (dehydrate).

The present disclosure will be illustrated using the following non-limiting examples/studies.

Studies

In the following examples these abbreviations are used: h=hours; min=minutes; p.o.=per oro (by mouth); t.i.d.=ter in die (3 times daily); s.e.=standard error; EV=empty vector; αSYN=alpha synuclein; $TH^{+ve}$=tyrosine hydroxylase positive; w/v=weight/volume; AP=anterior/posterior; DV=dorsal/ventral; AAV1/2=adeno-associated virus 1/2; LC-MS/MS=liquid chromatography tandem mass spectrometry; BLQ=below limit of quantification; $C_{max}$=The peak concentration of a drug after administration; $T_{max}$=time to reach maximum concentration; AUC=area under the curve; $t^{1/2}$=elimination half-life; CSF=cerebrospinal fluid.

EXAMPLE 1

The following example shows that trehalose is more efficacious at reducing parkinsonian symptoms in a rodent model of PD when trehalose is administered as a single, oral administration (2.67 g/kg/day) compared to when the same amount of trehalose is administered as three separate doses administered 8 h apart (0.89 g/kg/t.i.d.) or provided ad libitum in the drinking water (2% trehalose w/v in sterile water).

Thirty female, Sprague-Dawley rats (280-325 g) split into 5 groups (N=4-8 rats/group) and received a unilateral injection in to the substantia nigra (at co-ordinates AP −5.2 mm; ML −2 mm relative to Bregma, DV −7.5 mm relative to skull over SN) of AAV1/2 delivering A53T alpha-synuclein (AAV1/2 αSYN) or empty vector (control). The A53T αSyn expressed is of the human sequence. Its control is an empty AAV1/2 vector of the same serotype and viral construction. Both AAV1/2 vectors were diluted in sterile phosphate buffered saline and administered at a volume of 2 μl. The concentration of AAV1/2 used was $1.7\times10^{12}$ genomic particles/ml, which produces significant behavioural and dopaminergic nigrostriatal deficits between 3 and 6 weeks following surgical delivery (Koprich et al., PLoS One, 2011, DOI 10.1371/journal.pone.0017698).

Commencing on the day of surgery and continuing for 6 weeks, rats received either vehicle (sterile drinking water) or trehalose (2.67 g/kg/day) administered either in the drinking water (2% w/v), as three separate doses administered 8 h apart (0.89 g/kg/t.i.d., p.o.) or as a single administration (2.67 g/kg/day, p.o).

Animal behavior was assessed pre-surgery and at 3 and 6 weeks post-surgery. Behaviour was assessed by the cylinder test to assess forelimb asymmetry with asymmetry indicating an imbalance in striatal dopaminergic function between the side injected with AAV1/2 αSYN and the contralateral side. Compounds that normalize the forelimb asymmetry are potentially useful for treating PD. After 6 weeks of trehalose treatment, the animals were killed approximately 30 mins after the last administration of trehalose. Striatal tissue from both hemispheres was collected and analysed for dopamine levels. Substantia nigra tissue was collected and analysed for the number of $TH^{+ve}$ cells and the amount of A53T αSYN measured. Plasma and brain (cerebellum) samples were collected and trehalose levels analysed by LC-MS/MS.

Rats receiving A53T αSYN exhibited an increased asymmetry, and indication of parkinsonism, as measured by the cylinder test on both Day 21 and Day 42 compared to rats receiving EV (Table 2). Administration of trehalose as a single daily oral administration (2.67 g/kg/day, p.o) for 21 or 42 days reduced the asymmetry compared to mice receiving A53T αSYN alone to a level similar to rats receiving EV (Table 2). When the same daily dose of trehalose (2.67 g/kg/day) was administered as 3 doses, 8 h apart (0.89 g/kg/t.i.d., p.o) or provided ad libitum as a 2% w/v solution in the drinking water, there was no significant change in the level of asymmetry on either day 21 or day 42 (Table 2).

TABLE 2

Effect of A53T αSYN and trehalose on forelimb asymmetry in rats

| | % asymmetry (mean ± s.e.mean) | |
|---|---|---|
| Group | Day 21 | Day 42 |
| Empty vector control | 7.7 ± 9.4 | 14.9 ± 7.4 |
| A53T αSYN | 51.0 ± 14.8* | 52.4 ± 20.6 |
| A53T αSYN + 2% trehalose in drinking water | 48.1 ± 7.0* | 51.9 ± 11.9 |
| A53T αSYN + trehalose (0.89 g/kg, 3 times per day) | 38.9 ± 16.3 | 67.9 ± 11.1* |
| A53T αSYN + trehalose (2.67 g/kg, once per day) | 12.3 ± 16.9 | 3.8 ± 14.5# |

Mean ± s.e.mean.
* = P < 0.05 vs. EV control,
# = P < 0.05 vs. A53T aSYN.
One-way ANOVA followed by Fisher's LSD post-hoc test.

Rats receiving A53T αSYN also exhibited a significantly lower striatal dopamine level compared to rats receiving EV (Table 3). Administration of trehalose as a single daily oral administration (2.67 g/kg/day) partially, but significantly, restored striatal dopamine levels (Table 3). Administration of the same daily dose of trehalose (2.67 g/kg/day) as either 3 doses, 8 h apart (0.89 g/kg/day, t.i.d., p.o) or provided ad libitum as a 2% w/v solution in the drinking water, did not significantly alter striatal dopamine levels (Table 3).

TABLE 3

Effect of A53T αSYN and trehalose on striatal dopamine levels in rats

| Group | Dopamine (ng/mg protein) |
|---|---|
| Empty vector control | 123.8 ± 6.8 |
| A53T Asyn | 42.4 ± 5.8* |
| A53T αSYN + 2% trehalose | 60.2 ± 11.5* |

TABLE 3-continued

Effect of A53T αSYN and trehalose on striatal dopamine levels in rats

| Group | Dopamine (ng/mg protein) |
|---|---|
| in drinking water | |
| A53T αSYN + trehalose | 47.3 ± 7.5* |
| (0.89 g/kg, 3 times per day) | |
| A53T αSYN + trehalose | 65.4 ± 7.5*# |
| (2.67 g/kg, once per day) | |

Mean ± s.e.mean.
* = P < 0.05 vs. EV control,
# = P < 0.05 vs. A53T αSYN.
One-way ANOVA followed by Fisher's LSD post-hoc test.

As expected the amount of A53T αSYN per $TH^{+ve}$ neuron increased in rats receiving A53T αSYN compared to rats receiving EV (Table 4). Administration of trehalose as a single daily oral administration (2.67 g/kg/day, p.o) reduced the amount of A53T αSYN per $TH^{+ve}$ neuron compared to rats receiving A53T αSYN alone (Table 4). Administration of the same daily dose of trehalose provided ad libitum as a 2% w/v solution in the drinking water, did not significantly alter the amount of A53T αSYN per $TH^{+ve}$ neuron compared to rats receiving A53T αSYN alone (Table 4).

TABLE 4

Effect of A53T αSYN and trehalose on A53T αSYN expression per TH neuron in rats

| Group | aSYN/TH ratio |
|---|---|
| Empty vector control | 0.00000 ± 0.00000 |
| A53T αSYN | 0.00027 ± 0.00010* |
| A53T αSYN + 2% trehalose in drinking water | 0.00023 ± 0.00007* |
| A53T αSYN + trehalose (2.67 g/kg, once per day) | 0.00016 ± 0.00008 |

Mean ± s.e.mean.
* = P < 0.05 vs. EV control.
One-way ANOVA followed by Fisher's LSD post-hoc test.

Together, these data demonstrate that administering trehalose as a single bolus dose is more efficacious at removing αSYN, maintaining striatal dopamine levels and reducing behavioural impairments compared to the same dose of trehalose administered as 3 separate doses 8 h apart or administered over a 24 h period in the drinking water.

When the animals were killed 30 mins post trehalose administration plasma and brain samples were collected (rats in the 0.89 g/kg/day group only received one dose of trehalose (0.89 g/kg) on this day). This time corresponds to approximately the $T_{max}$ of orally administered trehalose. Trehalose plasma levels were below the limit of quantification (BLQ) in rats receiving trehalose in the drinking water (Table 5). Trehalose was measurable in the plasma 30 mins after receiving trehalose (0.89 or 2.67 g/kg) by oral gavage (Table 5). A 3-fold increase in the trehalose dose (0.89 g/kg to 2.67 g/kg) lead to an ~6-fold increase in the trehalose plasma level, i.e. that increasing the dose produced a greater than dose-proportional increase in trehalose exposure. Trehalose levels were below the limit of detection in the brain of rats receiving trehalose either in the drinking water or receiving trehalose (0.89 g/kg) by oral gavage (Table 5). Trehalose was measurable in the brains of rats receiving trehalose (2.67 g/kg) by oral gavage (Table 5).

TABLE 5

Plasma and brain trehalose levels after trehalose was administered in drinking water of via oral gavage

| Group | Trehalose administered | Plasma trehalose level (ng/ml) | Brain trehalose level (ng/g) |
|---|---|---|---|
| 1 | 2% in drinking water | BLQ | BLQ |
| 2 | 0.89 g/kg 3 times daily | 1131 ± 178 ng/ml | BLQ |
| 3 | 2.67 g/kg once daily | 6383 ± 890 ng/ml | 52.8 ± 16.9 ng/g |

Mean ± s.e.mean.
BLQ, below level of quantification

These data demonstrate that increasing the dose of trehalose produces a greater than dose-proportional increase in systemic exposure. This increased systemic exposure also allows detectable levels of trehalose to occur in the brain. The brain is the target organ of trehalose as a treatment for PD and these results provide an explanation as to why a single bolus administration of trehalose is more efficacious compared to the same dose of trehalose administered as three separate doses 8 h apart or administered over a 24 h period in the drinking water (Tables 2-4).

EXAMPLE 2

The following example shows the plasma and brain pharmacokinetics of trehalose on day 1 and day 7 in Sprague Dawley rats following oral administration of trehalose (2.67 g/kg/day) for 7 days. It shows that the plasma and brain samples taken for bioanalysis in Example 1 (30 minutes post-dose) was close to the $T_{max}$. It also shows that plasma levels and brain levels of trehalose quickly drop and are no longer detectable 8 h post-dose. These results thus support and expand upon the bioanalytical data presented in Example 1.

One hundred Sprague-Dawley rats (200-260 g), female (60) and male (40), received trehalose (2.67 g/kg/day, oral gavage in sterile water) for 1 or 7 days. Groups of 5 rats (3 female, 2 male) were sacrificed at pre-dose and 15 min, 30 min, 1 h, 1.5 h, 2 h, 3 h, 4 h, 8 h and 12 h post-dose on days 1 and 7 and plasma and brain samples collected. Plasma and brain samples were analysed for trehalose levels using a validated LC-MS/MS method and plasma exposure time-courses (FIG. 1) and pharmacokinetic parameters were calculated (Table 6). Brain levels of trehalose were approximately 1% of plasma levels at all time-points (FIG. 1).

TABLE 6

Plasma and brain pharmacokinetics of trehalose following 1 and 7 days oral administration of trehalose (2.67 g/kg)

| | Plasma | | Brain | |
|---|---|---|---|---|
| PK parameter | Day 1 | Day 7 | Day 1 | Day 7 |
| $T_{max}$ (h) | 0.25 | 0.25 | 0.25 | 0.25 |
| $C_{max}$ (ng/ml) | 8900 | 8336 | 87.0 | 73.0 |
| $AUC_{0-12h}$ (h · ng/ml) | 10851 | 9494 | 86.8 | 65.3 |
| $AUC_{0-inf}$ (h · ng/ml) | 11136 | 9876 | 97.0 | 76.2 |
| $t_{1/2}$ (h) | 0.76 | 0.89 | 0.81 | 1.06 |

EXAMPLE 3

The following example shows the plasma and brain pharmacokinetics of trehalose on day 1 and day 7 in female macaques following oral administration of trehalose (2.67 and 5.34 g/kg/day) for 7 days. It shows that in macaques, as in rats, increasing the dose of trehalose leads to a greater that dose-proportional increase in plasma trehalose level. As this occurs in two mammalian species, it is likely that it will also occur in a third mammalian species (humans). Therefore, in humans, administration of trehalose as a single daily oral dose is likely to produce higher systemic exposure and brain levels of trehalose than the same daily dose administered as multiple doses over 24 h and thus provide greater therapeutic benefit.

Three female macaques (3.81-4.67 kg) received trehalose (2.67 and 5.34 g/kg/day, oral gavage in sterile water) for 7 days. Plasma samples were collected pre-dose and 15 min, 30 min, 1 h, 2 h, 4 h, 6 h, 12 h and 24 h post-dose on days 1 and 7 and analysed for trehalose levels using a validated LC-MS/MS method and plasma exposure time courses (FIG. 2) and pharmacokinetic parameters were calculated (Table 7).

TABLE 7

Plasma pharmacokinetics of trehalose following 1 and 7 days oral administration of trehalose (2.67 and 5.34 g/kg)

| PK parameter | 2.67 g/kg/day | | 5.34 g/kg/day | |
| --- | --- | --- | --- | --- |
| | Day 1 | Day 7 | Day 1 | Day 7 |
| $T_{max}$ (h) | 0.83 | 0.67 | 0.67 | 0.83 |
| $C_{max}$ (ng/ml) | 10918 | 9578 | 36962 | 22444 |
| $AUC_{0-24h}$ (h · ng/ml) | 26657 | 26023 | 78899 | 56483 |
| $AUC_{0-inf}$ (h · ng/ml) | 27445 | 27363 | 80040 | 57172 |
| $t_{1/2}$ (h) | 1.1 | 1.5 | 1.8 | 2.3 |

In a subsequent step, the same 3 macaques were administered trehalose (2.67 g/kg) for two days. The macaques were then killed 1 h post-administration on day 2 and terminal brain and CSF samples collected. The brain and CSF trehalose levels were 81.3±13.8 ng/g and 562±346.5 ng/ml respectively. Similar to rats, trehalose levels in macaque brain tissue were ~1% of the plasma level at the corresponding timepoint.

EXAMPLE 4

The following example shows that trehalose can reduce dysfunction of the dopaminergic system in a non-human primate model of PD when trehalose is administered as a single, oral administration (2.67 g/kg/day). Moreover, the dose of trehalose used provided exposure levels similar to the exposure that was demonstrated to be efficacious in a rodent model of PD (see Examples 1 and 3).

Twenty-five (25), female cynomolgus monkeys (Macaca fascicularis, 8.0-9.3 years of age, 3.2-4.4 kg) were split into 3 groups (n=8-9/group) and received stereotaxic injection of AAV vectors,either a vector expressing mutant A53T human alpha-synuclein (AAV1/2-A53T-alpha-synuclein) or an empty vector (AAV1/2-EV), Genedetect, Auckland, New Zealand) into the substantia nigra. The A53T aSyn expressed is of the human sequence the AAV1/2-EV is a control vector of the same serotype and viral construction. Precise stereotaxic coordinates for all surgeries were calculated prior to surgery from individual monkey MRI scans. Injections containing the AAV1/2-A53T-alpha-synuclein or empty vector were made at a speed of 0.5 µl/min and a volume of 7 µl (at a viral titre of $1.7 \times 10^{12}$ active particles per ml) into 4 sites of each hemisphere of the substantia nigra. Commencing on the day of surgery and continuing for 17 weeks, macaques received either vehicle (sterile drinking water) or trehalose (2.67 g/kg/day) administered as a single daily administration (2.67 g/kg/day, p.o). The macaques were then killed and striatal tissue from both hemispheres was collected and analysed for dopamine and dopamine transporter (DAT) levels. Substantia nigra tissue was collected and analysed for the number of $TH^{+ve}$ cells and the amount of αSYN measured. Plasma, CSF and brain (cerebellum) samples were collected and trehalose levels analysed by LC-MS/MS.

Macaques receiving A53T exhibited a significantly lower striatal dopamine and DAT levels compared to macaques receiving EV (Table 8). Administration of trehalose as a single daily oral administration (2.67 g/kg/day) partially, but significantly, restored striatal dopamine levels (Table 8). Similarly, trehalose partially restored DAT levels (Table 8).

TABLE 8

Effect of A53T αSYN and trehalose on striatal dopamine and DAT levels in macaques

| Group | Striatal dopamine (ng/mg protein) | Striatal DAT (nCi/mg tissue) |
| --- | --- | --- |
| Empty vector control | 160.0 ± 7.2 | 493.7 ± 52.5 |
| A53T αSYN | 78.9 ± 13.1*** | 273.7 ± 35.7** |
| A53T αSYN + trehalose (2.67 g/kg/day) | 110.0 ± 8.3** # | 410.7 ± 47.9 |

Mean ± s.e.mean.
/* = P < 0.01 or P < 0.001 cf. EV/vehicle.
# = P < 0.05 cf. αSyn/vehicle, 1-way ANOVA with Holm-Sidak multiple comparisons test.

Macaques receiving A53T also exhibited fewer $TH^{+ve}$ neurons in the substantia nigra and an increased expression of αSYN in the striatum compared to macaques receiving EV (Table 9). Administration of trehalose as a single daily oral administration (2.67 g/kg/day, p.o) only slightly prevented the loss of $TH^{+ve}$ neurons and increase in αSYN (Table 9).

TABLE 9

Effect of A53T αSYN and trehalose on $TH^{+ve}$ neurons in the substantia nigra and aSYN expression in the striatum levels in macaques

| Group | No. of TH+ve neurons | Striatal αSYN (ng/mg protein) |
| --- | --- | --- |
| Empty vector control | 95678 ± 7799 | 36394 ± 2362 |
| A53T αSYN | 59513 ± 7720* | 55455 ± 5120* |
| A53T αSYN + trehalose (2.67 g/kg/day) | 69084 ± 7628* | 54604 ± 4486* |

Mean ± s.e.mean.
* = P < 0.01 cf. EV/vehicle.
1-way ANOVA with Holm-Sidak multiple comparisons test.

Together, these data demonstrate that trehalose can partially prevent αSYN-mediated dopaminergic dysfunction though this effect is more pronounced at the nerve terminals than at the cell bodies, as demonstrated by a larger effect on dopamine and DAT compared to the effect on the number of $TH^{+ve}$ neurons.

Figure 4:
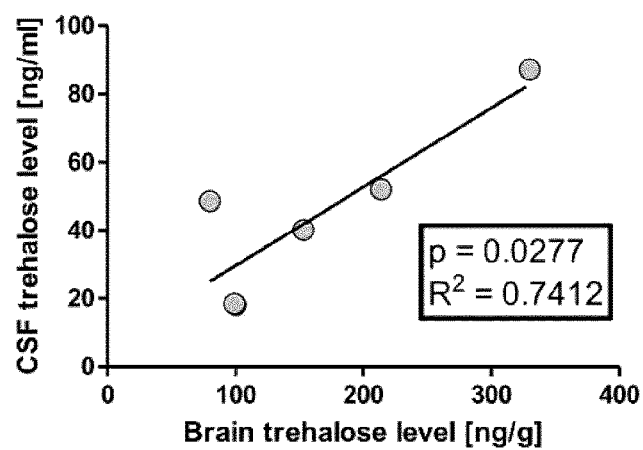
FIG. 4 shows the correlation between trehalose levels in the CSF and brain of macaques following 17 weeks of oral administration of trehalose (2.67 g/kg/day, p.o. administered as a single bolus dose).

Single plasma, brain and CSF samples were collected 1 h after the final administration of trehalose. One-hour post-dose corresponds to approximately the $T_{max}$ of orally administered trehalose in macaques. The plasma, brain and CSF trehalose levels were 2449±884 ng/ml, 129±35 ng/g and 33±9 ng/ml respectively. The trehalose level in the CSF significantly correlated with the level in the brain demonstrating that trehalose levels in the CSF can be used to predict trehalose levels in the brain (FIG. 4).

Results

The results for the behavioural assessment in rats on days 21 and 42 are shown in Table 2. The αSYN (PD model)

group showed an increased asymmetry compared to the empty vector (control group). The degree of asymmetry is indicative of an imbalance in striatal dopaminergic function between the side the viral vector that produces αSYN was administered and the contralateral side. Compounds that normalize the forelimb asymmetry are potentially useful for treating PD. Treatment with trehalose as a single, oral administration (2.67 g/kg/day as a single dose group) reduced the degree of asymmetry compared to mice receiving A53T αSYN alone, indicating that trehalose given as a single daily administration was normalising behaviour. By contrast, the same daily dose of trehalose administered either as 2% in the drinking water or when given as three (3) separate doses, 8 h apart did not produce a beneficial effect on behaviour.

Dopamine is the neurotransmitter that is decreased both in PD and in animal models of PD. Increasing striatal dopamine levels is a treatment for PD and also reverses the parkinsonism seen in this rat model of PD. Therefore, if trehalose (single administration) increases dopamine levels it provides a rationale for how it is improving behaviour.

As can be seen from Table 3, when trehalose is given as a once daily, single administration it significantly increases dopamine levels compared to animals receiving αSYN alone. Interestingly, when the same total dose of trehalose is administered either in the drinking water or divided into three (3) times daily administrations, the increase in dopamine levels is smaller and no longer significantly different from αSYN alone.

These results support the behavioural data; trehalose given once a day increases dopamine levels as well as reducing the degree of asymmetry. In addition, they provide a rationale why trehalose administered in other ways (2% in the drinking water or three (3) times daily) did not improve behaviour (they did not increase dopamine levels).

Referring to Table 4, when the amount of αSYN per TH$^{+ve}$ neuron was measured there was a clear increase in the α-synuclein per neuron in the PD model group compared to the empty vector control group. Treatment with trehalose once daily reduced the amount of α-synuclein per neuron by ~40%. Trehalose in the drinking water produced only a small reduction in the amount of α-synuclein per neuron.

This result supports the hypothesis that trehalose reduces the amount of α-synuclein. It also further supports the idea that administering all the trehalose in one dose is more efficacious that administrating the same amount of trehalose over a 24 hour period.

Pharmacokinetics of Trehalose in Rats

To better understand why administrating the same amount of trehalose by different routes led to differences in efficacy, studies were conducted to measure blood and brain levels of trehalose following administration of trehalose by 2% in the drinking water, three (3) times daily (0.89 g/kg each dose) and once daily (2.67 g/kg/day). Plasma samples were collected at 30 min post dose (around the T$_{max}$) so that rats either received whatever trehalose they had drunk in the water in the previous 24 h, 0.89 g/kg or 2.67 g/kg. The results are shown in Table 5.

There are several observations of note in the results, which are listed below.
1. That trehalose in the drinking water did not produce any measurable trehalose levels in the plasma and brain. Although we do not know when the rats last drank relative to when the blood was collected it provides an explanation of why trehalose administered in the drinking water was not effective.
2. That trehalose (0.89 g/kg 3×/day) produced measurable levels of trehalose in the plasma but did not produce measurable brain trehalose levels.
3. That trehalose (2.67 g/kg 1×/day) produced measurable levels of trehalose in the plasma and the brain.
4. That the peak plasma trehalose level following 2.67 g/kg was 5.6-fold higher than the plasma trehalose level following 0.89 g/kg. That is, a 3-fold increase in dose led to a 5.6-fold increase in systemic trehalose exposure.

Full Pharmacokinetic Study in Rats

A full pharmacokinetic study was performed in rats following 1 and 7 days administration of trehalose (2.67 g/kg/day given as a single administration) and the results are summarized in FIG. 1 and Table 6.

As can be seen, trehalose is rapidly absorbed into, and rapidly eliminated from, the plasma following oral administration. No trehalose is found in the plasma or brain 8 h post-dose. This is important as in the efficacy study the group receiving 3 administrations of trehalose were given 8 h apart and so plasma trehalose levels had declined to below the limit of detection between each subsequent trehalose administration. Brain trehalose levels represent approximately 1% of plasma levels and brain levels follow a very similar time-course to plasma levels.

Pharmacokinetics of Trehalose in Non-Human Primates

Figure 2:
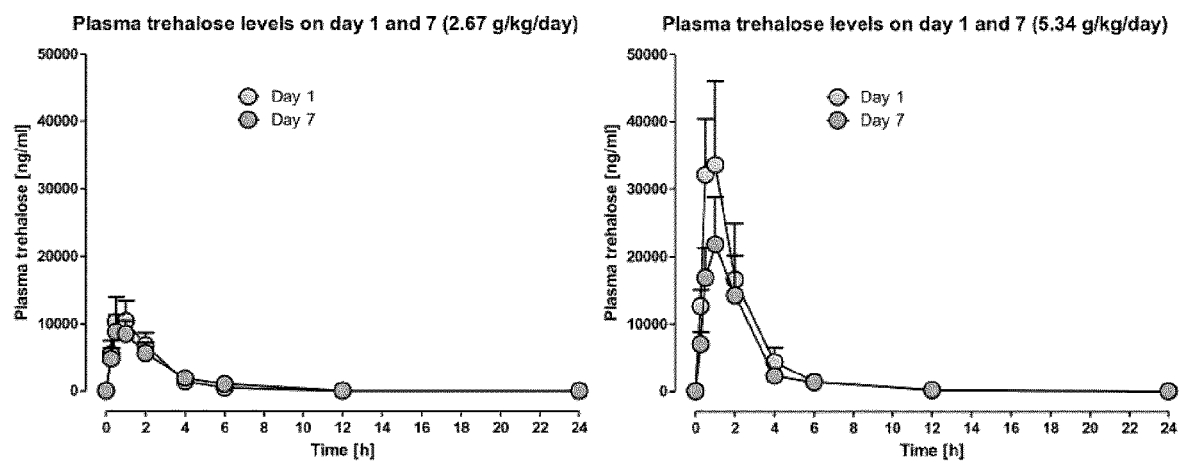
FIG. 2 shows the timecourse of trehalose exposure in the plasma of macaques following 1 and 7 days oral administration of trehalose (2.67 g/kg/day and 5.34 g/kg/day, p.o. administered as a single bolus dose).

A full pharmacokinetic study was performed in macaques following 1 and 7 days administration of trehalose (2.67 or 5.34 g/kg/day given as a single administration) and the results are summarized in FIG. 2 and Table 7.

Similar to rats, trehalose is rapidly absorbed into, and rapidly eliminated from, the plasma following oral administration to macaques. No trehalose was measurable in the plasma ~8 h post-dose. Also similar is that a doubling of the dose of trehalose led to an approximately 3-fold increase in plasma trehalose levels (as measured by C$_{max}$ or AUC)— again showing that increasing the dose produces a greater than expected increase in plasma levels.

Brain and CSF levels of trehalose were also measured following 2 days administration of trehalose (2.67 g/kg). Brain and CSF samples were collected 1 h post-dose (approximately the plasma T$_{max}$) and brain and CSF trehalose levels were 81.3±13.8 ng/g and 562±346.5 ng/ml respectively. Therefore, the brain trehalose levels represent approximately 1% of plasma levels, which is similar to rats.

Efficacy of Trehalose in Non-Human Primates

As can be seen from Table 8 when trehalose is administered once daily to non-human primates it significantly increases dopamine levels compared to animals receiving αSYN alone. This result is very similar to the result obtained in rats (compare Tables 3 and 8).

This result, along with the finding that the same dose of trehalose on a g/kg basis provides a similar plasma trehalose exposure, supports the hypothesis that a dose of trehalose that provides a similar trehalose exposure in rats and non-human primates also significantly reduces αSYN-induced striatal dopamine loss in both species. Together, these results suggest that an equivalent dose, on a g/kg basis, of trehalose produces similar trehalose exposures in the plasma and brain of rats and non-human primates and that this exposure also produces similar efficacious effects in rats and non-human primates. As these effects are preserved between rats and non-human primates it is also likely that they will translate to humans with Parkinson's disease and this allows us to estimate a dose of trehalose that is likely to be efficacious in treating Parkinson's disease.

Extrapolating From Animal Data to a Human Dose

Figure 3:
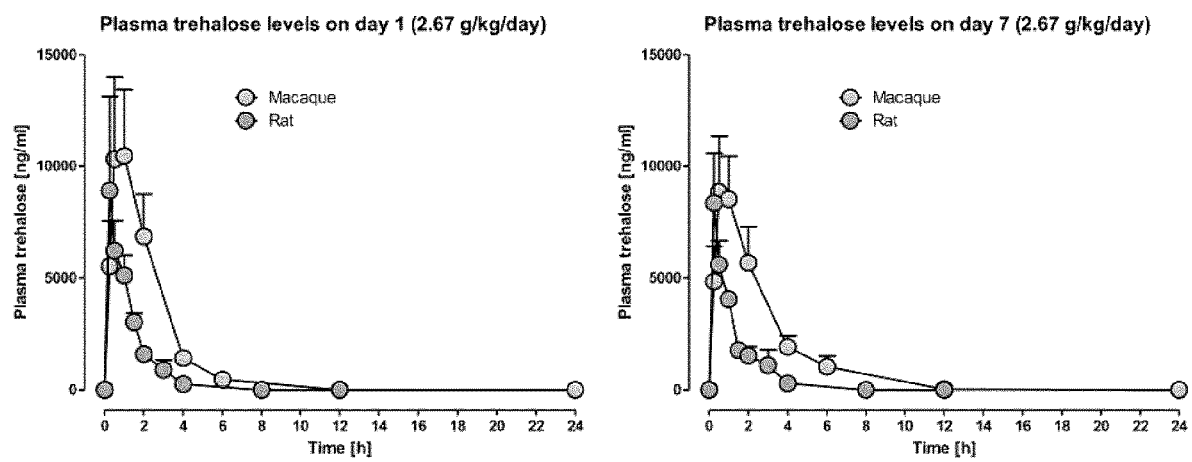
FIG. 3 shows the comparative timecourse of trehalose exposure in the plasma of rats and macaques following 1 and 7 days oral administration of trehalose (2.67 g/kg/day, p.o. administered as a single bolus dose).

On a dose per body weight basis, trehalose produced very similar plasma and brain levels in rats and macaques (see FIG. 3 and Tables 6 and 7) when dosed with 2.67 g/kg/day. We also know that a trehalose dose of 2.67 g/kg/day was efficacious in the rat and non-human primate. Therefore, it is contemplated that an efficacious dose for humans includes 2.67 g/kg which is estimated to produce a trehalose plasma $C_{max}$ of ~10000 ng/ml. From the rat data it is also clear that a dose of 0.89 g/kg will be ineffective.

Therefore, if we assume the average human weight is 80 kg then based on the results disclosed herein, it is estimated that 214 g/day would be an efficacious dose. Similarly, it is contemplated that a dose below 71 g/day will not be efficacious in human. Table 10 below shows the required daily dosages for the various weight ranges.

TABLE 10

| Body weight (kg) | Required daily trehalose (g) |
|---|---|
| Up to 50 | 130 |
| 51-60 | 160 |
| 61-70 | 190 |
| 71-80 | 210 |
| 81-90 | 240 |
| 91-100 | 270 |
| 101-110 | 300 |
| Over 110 | 330 |

The trehalose may be formulated as a pharmaceutical composition for treating neurological disorders, comprising a daily dose of trehalose, and a pharmaceutically acceptable composition wherein the daily dose of the trehalose is between about 0.25 to about 12.5 g/kg. Examples of pharmaceutical acceptable compositions include carriers, diluents, adjuvants, excipients or vehicles, preserving agents, fillers, disintegrating agents, buffering agents, penetration enhancers, wetting agents, emulsifying agents, suspending agents, sweetening agents, flavouring agents, perfuming agents, antibacterial agents, antifungal agents, lubricating agents and dispensing agents. Suitable dosage forms include, for example, tablets, dragees, powders, elixirs, syrups, liquid preparations including suspensions and emulsions, lozenges, granules and capsules. Techniques and formulations generally may be found in Remington, Pharmaceutical Sciences, Mack Publishing Co., Easton, Pa., latest edition.

The trehalose may be incorporated into a "foodstuff", "food supplement", "beverage" or "beverage supplement" composition, where "foodstuff", "food supplement", "beverage" or "beverage supplement" have normal meanings for those terms and are not restricted to pharmaceutical preparations, for treating neurological disorders, comprising a daily dose of trehalose, and a dietary acceptable carrier wherein the daily dose of the trehalose is between about 0.25 to about 12.5 g/kg. In an embodiment of the daily dose is about 2.67 g/kg/day.

The present disclosure provides a pharmaceutical kit comprising:
trehalose for treatment of neurological disorders, and
instructions for a single daily administration of the trehalose with the daily dose being between about 0.25 to about 12.5 g/kg/day.

In some embodiments of the pharmaceutical kit the daily dose is between about 0.5 to about 10 g/kg/day.

In some embodiments of the pharmaceutical kit the daily dose is between about 0.75 to about 7.5 g/kg/day.

In some embodiments of the pharmaceutical kit the daily dose is one of between about 1 to about 5 g/kg/day and about 1.25 to about 3.75 g/kg/day.

In an embodiment of the pharmaceutical kit the daily dose is about 2.67 g/kg/day.

The pharmaceutical kit may include the following instructions:

| Body weight (kg) | Required daily trehalose (g) |
|---|---|
| Up to 50 | 130 |
| 51-60 | 160 |
| 61-70 | 190 |
| 71-80 | 210 |
| 81-90 | 240 |
| 91-100 | 270 |
| 101-110 | 300 |
| Over 110 | 330 |

Translatability to Other Diseases

While the present studies have been focused on PD, it will be appreciated that for PD the studies have shown that trehalose administered as a single bolus dose is more efficacious than when administered throughout the day. It is therefore contemplated that these results may be applicable to diseases other than PD, especially those diseases where it has already been demonstrated that trehalose administered in the drinking water is efficacious (e.g. Alzheimer's disease, tauopathies, amyotrophic lateral sclerosis and Huntington's disease). It is contemplated that there are two (2) other 'groups' of diseases, in addition to PD, that may exhibit the same results as found with PD, namely synucleinopathies (diseases that have misfolded α-synuclein), and proteinopathies (diseases that have a misfolded protein other than α-synuclein). PD is a synucleinopathy and synucleinopathies are a subset of proteinopathies. In summary these diseases may include:
1. Parkinson's disease,
2. Synucleinopathies including (but not limited to), Parkinson's disease with dementia, dementia with Lewy bodies, MSA, essential tremor, Gaucher disease and other lysosomal storage disorders, neurodegeneration with brain iron accumulation, and
3. Other proteinopathies including (but not limited to), Alzheimer's disease, Cerebral β-amyloid angiopathy, Retinal ganglion cell degeneration in glaucoma, Prion diseases, Tauopathies, Frontotemporal lobar degeneration, FTLD-FUS, Amyotrophic lateral sclerosis (ALS), Huntington's disease and other triplet repeat disorders, Familial British dementia, Familial Danish dementia, Hereditary cerebral hemorrhage with amyloidosis, CADASIL, Alexander disease, Seipinopathies, Familial amyloidotic neuropathy, Senile systemic amyloidosis, Serpinopathies and Retinitis pigmentosa with rhodopsin mutations.

CONCLUSION

The present inventors have conducted studies to investigate the potential of trehalose to be developed as a treatment for various neurological disorders, including but not limited to Parkinson's disease. As part of these studies the inventors:
1) developed a quantitative method for measuring trehalose levels in plasma and brain tissues;
2) investigated the efficacy of three different ways of administrating the same dose of trehalose (in drinking water, administered as a single dose or administered as 3 doses eight hours apart).

3) investigated the plasma and brain pharmacokinetics of trehalose following oral administration of trehalose.

In summary the inventors have demonstrated the following.
1) When trehalose was given as a single administration it was much more efficacious than when the same amount of trehalose was administered in the drinking water or as 3 administrations, 8 hours apart.
2) That blood levels of trehalose are not dose linear. Increasing the dose 3-fold led to a 6 fold increase in trehalose plasma level in rats and a doubling of the dose led to a greater than 3-fold plasma exposure in macaques.
3) That trehalose only reached the brain in detectable amounts when the dose of trehalose was administered as a single bolus dose.

Taken together, these results demonstrate the very surprising result that trehalose is more efficacious when given as a single bolus dose. Without being bound by any hypothesis, the inventors contemplate that a reason for this enhanced efficacy may be that dosing all the trehalose in one administration leads to a greater systemic drug exposure than would be expected if the drug exhibited linear kinetics. The reason why this occurs is unknown but the inventors contemplate that it might be due to higher doses of trehalose saturating the systems that eliminate trehalose from the body.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A composition for treating neurological disorders in human patients, comprising a single oral daily dose of trehalose in a physiologically acceptable carrier wherein the single oral daily dose of the trehalose is between about 100 to about 1000 grams based on an 80 kilogram body weight of a human.

2. The composition according to claim 1, wherein the carrier is a pharmaceutically acceptable carrier.

3. The composition according to claim 1, wherein the carrier is foodstuff, foodstuff supplement, beverage or beverage supplement.

4. The composition according to claim 3, wherein the carrier is a calorific material comprising fats, oils, carbohydrates, proteins, or sources of minerals, vitamins or fiber or any combination thereof.

5. The composition according to claim 3, wherein the carrier is any one of dairy, cereal, vegetable, meat, fish, poultry, fruit based foodstuffs, processed foods, cooking ingredients and sweeteners.

6. The composition according to claim 3, wherein the carrier is any one of water, carbonated beverages, uncarbonated beverages, fruit juices, infusion drinks, coffee, teas, protein-shakes, soft-drinks or alcoholic drinks.

7. The composition according to claim 1 wherein the single oral daily dose is between about 100 to about 800 grams.

8. The composition according to claim 1 wherein the single oral daily dose is between about 100 to about 600 grams.

9. The composition according to claim 1 wherein the single oral daily dose is between about 100 to about 400 grams.

10. The composition according to claim 1 wherein the single oral daily dose is between about 100 to about 300 grams.

11. The composition according to claim 1 wherein the single oral daily dose is about 215 grams.

12. The composition according to claim 1 wherein the neurological disorders are any one or combination of Parkinson's disease, synucleinopathies and proteinopathies.

13. The composition according to claim 1 wherein the neurological disorder is Parkinson's disease.

14. The composition according to claim 12 wherein the synucleinopathy is any one of Parkinson's disease with dementia, dementia with Lewy bodies, MSA, essential tremor, Gaucher disease and other lysosomal storage disorders, and neurodegeneration with brain iron accumulation.

15. The composition according to claim 12 wherein the proteinopathies include Alzheimer's disease, cerebral β-amyloid angiopathy, retinal ganglion cell degeneration in glaucoma, prion diseases, tauopathies, frontotemporal lobar degeneration, FTLDFUS, amyotrophic lateral sclerosis (ALS), Huntington's disease and other triplet repeat disorders, familial British dementia, familial Danish dementia, hereditary cerebral hemorrhage with amyloidosis, CADASIL, Alexander disease, seipinopathies, familial amyloidotic neuropathy, serpinopathies and retinitis pigmentosa with rhodopsin mutations.

16. The composition according to claim 1 wherein the single oral daily dose of trehalose is in the following amount:

| Body weight (kg) | Amount of trehalose (g) |
| --- | --- |
| Up to 50 | 130 |
| 51-60 | 160 |
| 61-70 | 190 |
| 71-80 | 210 |
| 81-90 | 240 |
| 91-100 | 270 |
| 101-110 | 300 |
| Over 110 | 330. |

17. The composition according to claim 9 wherein the neurological disorders are any one or combination of Parkinson's disease, synucleinopathies and proteinopathies.

18. The composition according to claim 9 wherein the neurological disorder is Parkinson's disease.

19. A pharmaceutical kit comprising:
the composition according to claim 1, and
instructions for a single daily administration of the composition for treatment of neurological disorders.

20. The pharmaceutical kit according to claim 8, wherein the neurological disorders are any one or combination of Parkinson's disease, synucleinopathies and proteinopathies.

* * * * *

UNITED STATES PATENT AND TRADEMARK OFFICE
CERTIFICATE OF CORRECTION

PATENT NO. : 10,736,909 B2
APPLICATION NO. : 16/076468
DATED : August 11, 2020
INVENTOR(S) : Jonathan Michael Brotchie et al.

Page 1 of 1

It is certified that error appears in the above-identified patent and that said Letters Patent is hereby corrected as shown below:

In the Claims

Column 16, Line 27, Claim 15 should read:
"15. The composition according to claim 12 wherein the proteinopathies include Alzheimer's disease, cerebral β-amyloid angiopathy, retinal ganglion cell degeneration in glaucoma, prion diseases, tauopathies, frontotemporal lobar degeneration, FTLD-FUS, amyotrophic lateral sclerosis (ALS), Huntington's disease and other triplet repeat disorders, familial British dementia, familial Danish dementia, hereditary cerebral hemorrhage with amyloidosis, CADASIL, Alexander disease, seipinopathies, familial amyloidotic neuropathy, serpinopathies and retinitis pigmentosa with rhodopsin mutations."

Column 16, Line 58, Claim 20 should read:
"20. The pharmaceutical kit according to claim 19, wherein the neurological disorders are any one or combination of Parkinson's disease, synucleinopathies and proteinopathies."

Signed and Sealed this
Nineteenth Day of January, 2021

Andrei Iancu
*Director of the United States Patent and Trademark Office*